United States Patent [19]
Chen

[11] Patent Number: 6,003,235
[45] Date of Patent: Dec. 21, 1999

[54] FOLDING COLLAPSIBLE BODY-HEIGHT MEASURING GAUGE

[76] Inventor: Han-Liang Chen, 6-1Fl., No. 76, Ting-Tai St., Kaohsiung, Taiwan

[21] Appl. No.: 08/897,034

[22] Filed: Jul. 18, 1997

[51] Int. Cl.⁶ .................................................. G01C 5/107
[52] U.S. Cl. ................................ 33/512; 33/458; 33/515; 33/811
[58] Field of Search ................ 33/512, 511, 515, 33/832, 833, 458, 806, 810, 811; 403/102, 92, 93

[56] References Cited

U.S. PATENT DOCUMENTS

| | | | |
|---|---|---|---|
| 1,489,239 | 4/1924 | Eagan | 33/343 |
| 1,996,553 | 4/1935 | Scully | 33/512 |
| 3,137,943 | 6/1964 | Mechaneck | 33/2 R |
| 3,934,351 | 1/1976 | Sullivan | 33/458 |
| 3,955,285 | 5/1976 | Moeckl | 33/515 |
| 4,118,868 | 10/1978 | Johnson | 33/512 |

*Primary Examiner*—Andrew Hirshfeld
*Assistant Examiner*—Richard A. Smith
*Attorney, Agent, or Firm*—Bacon & Thomas PLLC

[57] ABSTRACT

A folding collapsible body-height measuring gauge including: a scale having a plurality of scale elements pivotably connected with one another in a series, each scale element having a coupling block at one end and a coupling open chamber at an opposite end for connection; a measurement indicator longitudinally slidably mounted on the scale; and a base having a coupling block at its one end adapted for supporting the scale in a vertical position for measuring the height of the body and two pivoted legs at its opposite end, the coupling block of the base having two coupling portions disposed at different elevations and adapted for coupling to the scale.

2 Claims, 7 Drawing Sheets

FOLDING COLLAPSIBLE BODY-HEIGHT MEASURING GAUGE

BACKGROUND OF THE INVENTION

The present invention relates to a body-height measuring gauge, and, more specifically, to a body-height measuring gauge that can be folded up into a collapsed manner when not in use.

A variety of body-height measuring instruments have been disclosed, and have appeared on the market. Examples of these body-height measuring instrument are seen in U.S. Pat. Nos. 4,134,212; 4,134,213; and 4,896,432. However, these body-height measuring instrument are usually heavy and not collapsible.

SUMMARY OF THE INVENTION

According to one aspect of the present invention, the folding collapsible body-height measuring gauge is comprised of a scale detachably supported on a base, and a measurement indicator slidably mounted on the scale, wherein the scale is comprised of a plurality of scale elements pivotably connected into a line that can be folded up when the gauge is not in use. According to another aspect of the present invention, the base has a coupling block with two coupling portions disposed at different elevations for coupling to the scale alternatively, so that the gauge can be arranged into two different forms for measuring the height of the body in a vertical manner or a horizontal manner.

DETAILED DESCRIPTION OF THE PREFERRED EMBODIMENT

Figure 1:
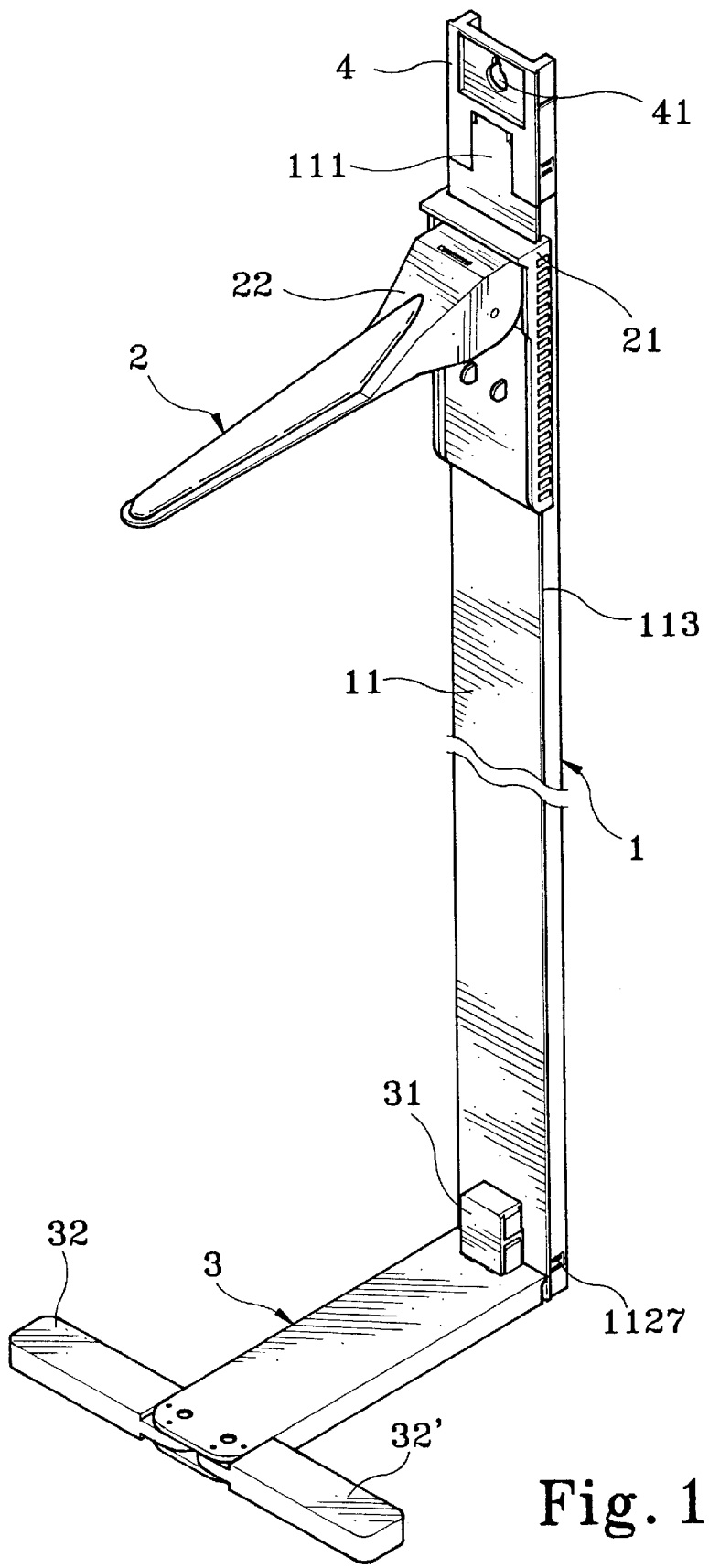
FIG. 1 is a perspective view of a folding collapsible body-height measuring gauge according to the present invention.

Referring to FIG. 1, a folding collapsible body-height measuring gauge in accordance with the present invention is generally comprised of a scale 1, a measurement indicator 2, a base 3, and a hanging block 4.

Figure 2:
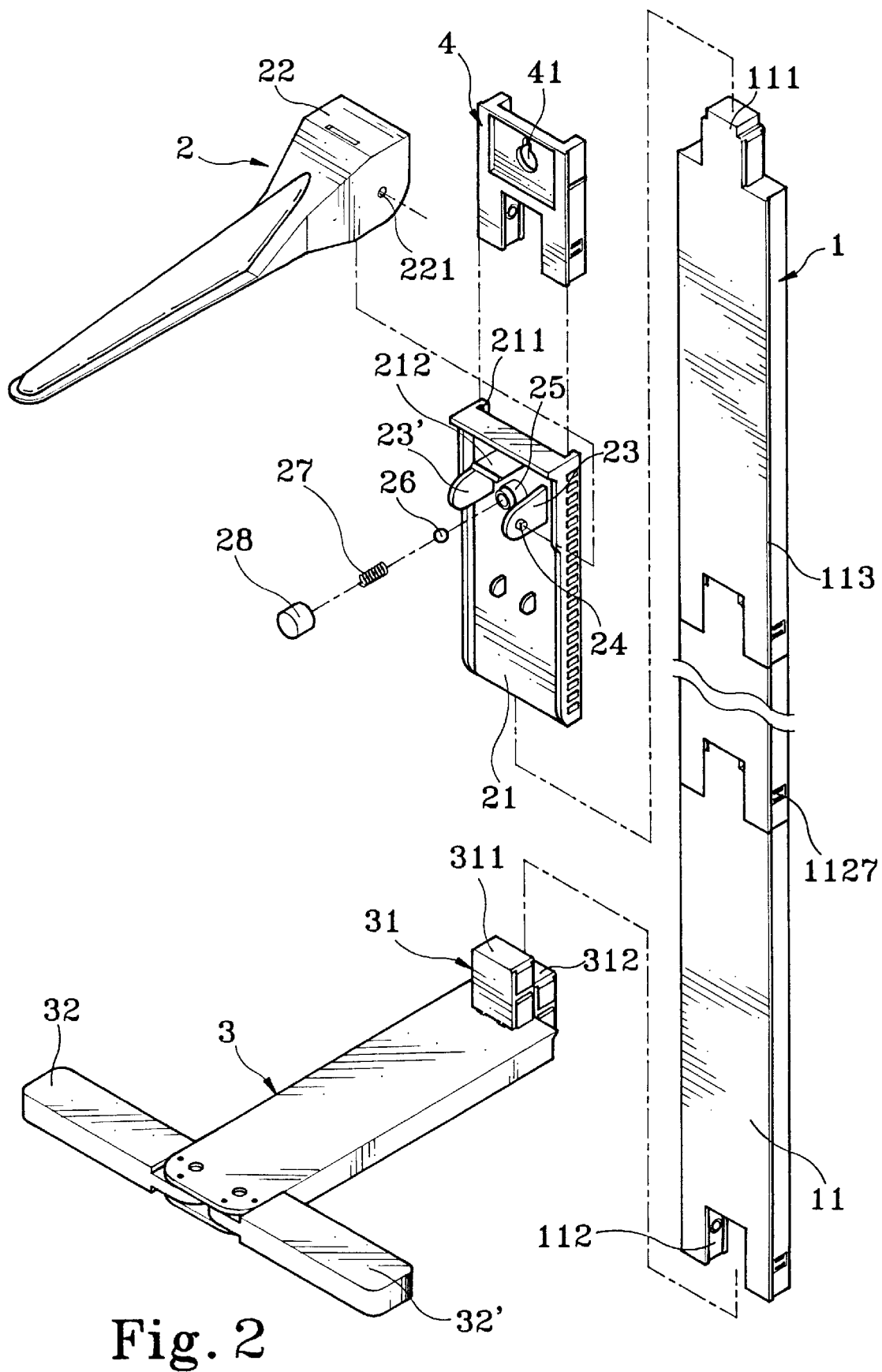
FIG. 2 is an exploded view of the folding collapsible body-height measuring gauge shown in FIG. 1.
Figure 3A:
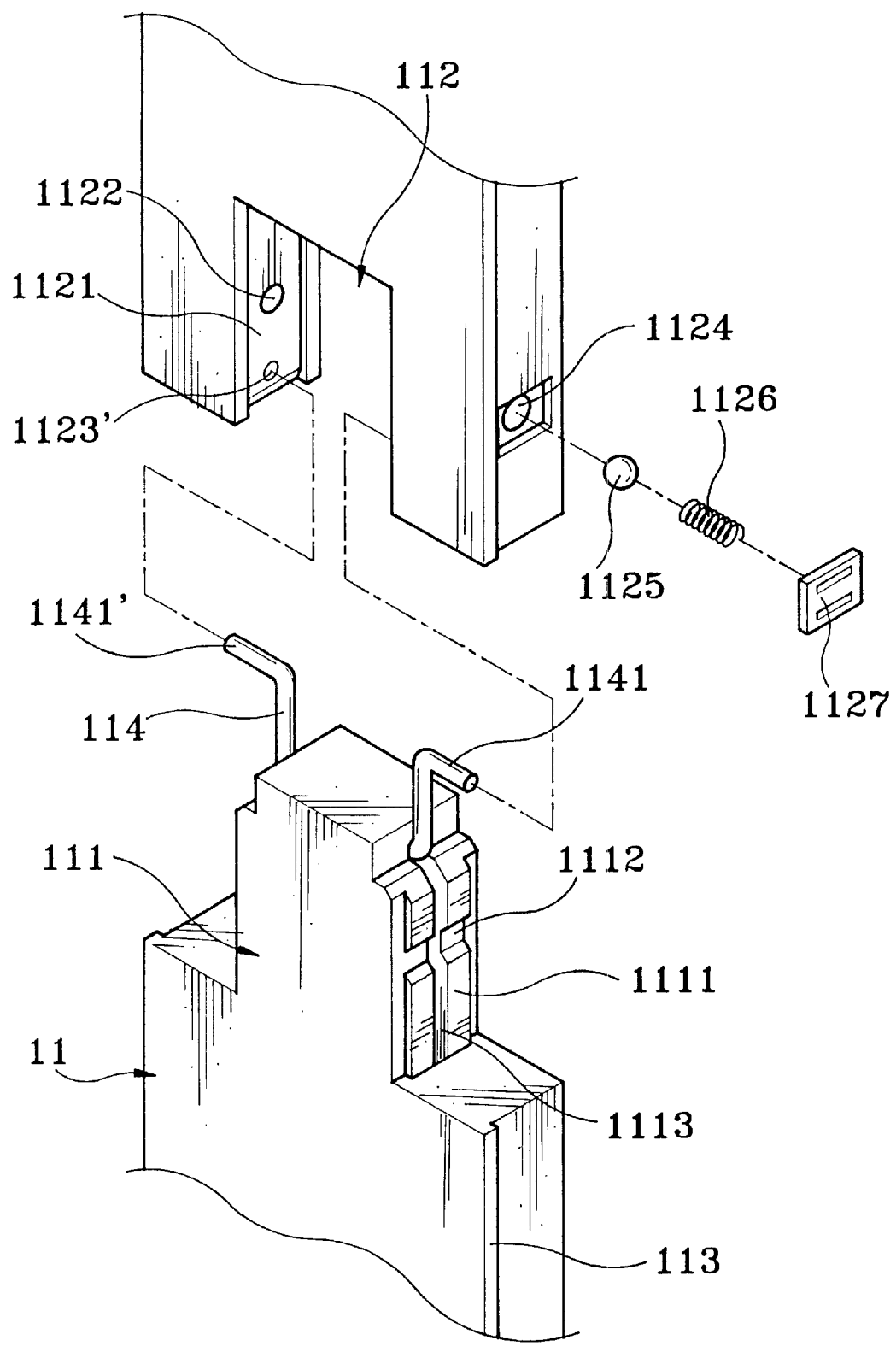
FIG. 3A is an exploded view in an enlarged scale of a part of the scale according to the present invention.
Figure 3C:
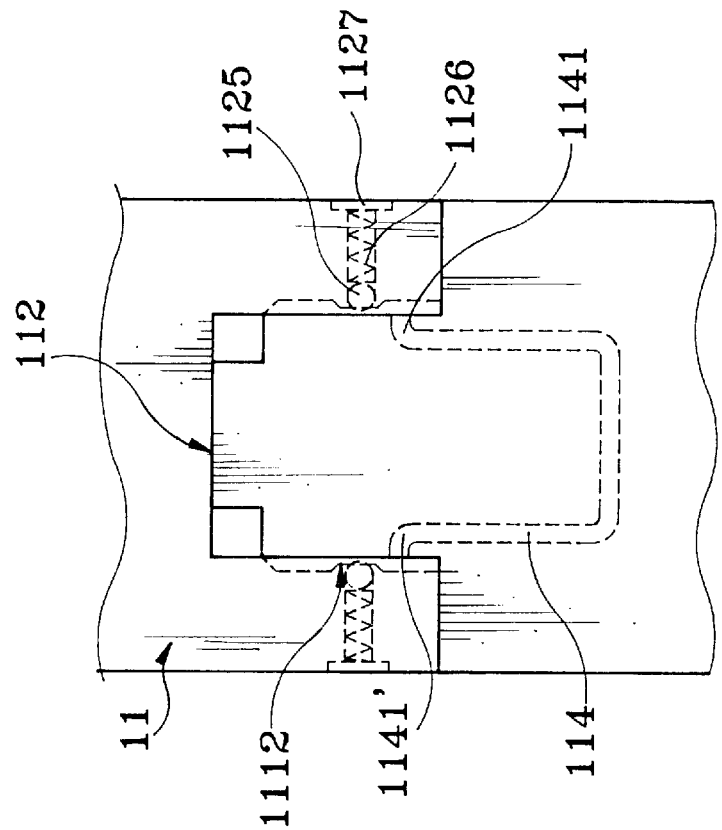
FIG. 3C is similar to FIG. 3B but showing the coupling tongues of the coupling block of the second scale element forced into engagement with the coupling grooves of the first scale element.
Figure 3B:
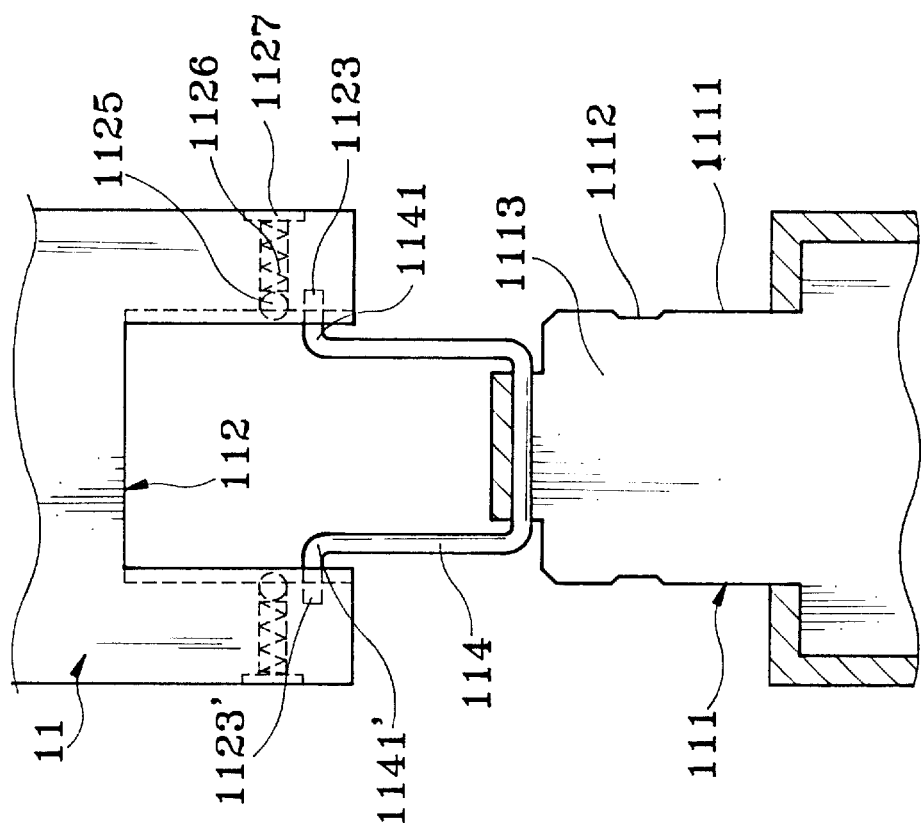
FIG. 3B is a schematic drawing showing the two end pieces of the hanging rod of a first scale element respectively fastened to the transverse coupling holes of a second scale element according to the present invention.

Referring to FIG. 2 and FIG. 1, the scale 1 is comprised of a plurality of scale elements 11 and is pivotably connected in series and coupled to one end of the base 3 with two longitudinal sliding tracks 113 bilaterally extending along its length. The measurement indicator 2 is coupled to the scale 1 and moved along the longitudinal sliding tracks 113. The hanging block 4 is coupled to one end namely the top end, of the scale 1 remote from the base 3.

Referring to FIGS. 3A, 3B, 3C and 4, and FIGS. 1 and 2, each scale element 11 of the scale 1 comprises a coupling block 111 longitudinally raised from its one end, a coupling open chamber 112 longitudinally from its opposite end, two longitudinal coupling tongues 1111 longitudinally raised from two opposite sides of the coupling block 111, a longitudinal sliding slot 1113 formed in the coupling block 111 and extending through the two longitudinal coupling tongues 1111, two transverse retaining grooves 1112 transversely disposed at two opposite sides of the coupling block 111 and respectively intersecting with the coupling tongues 1111, a substantially U-shaped hanging rod 114 movable in the sliding slot 1113 and having two opposite end pieces 1141 and 1141' horizontally extended outwards in reversed directions, two longitudinal coupling grooves 1121 longitudinally disposed within the coupling open chamber 112 at two opposite sides, two transverse coupling holes 1123 and 1123' respectively and transversely disposed in the longitudinal coupling grooves 1121 at an outer end, two retaining devices 1122 respectively mounted in the longitudinal coupling grooves 1121 and spaced above the transverse coupling holes 1123 and 1123'. Each retaining device 1122 comprises a socket 1124 transversely mounted in a hole (not shown) in one longitudinal coupling groove 1121, a cover plate 1127 fastened to one side of the scale element 11 to close an outer end of the socket 1124, a compression spring 1126 mounted in the socket 1124 and supported on the cover plate 1127, and a ball 1125 mounted in the socket 1124 and supported on the compression spring 1126 and forced by the spring force of the compression spring 1126 to partially project out of the socket 1124 into the coupling open chamber 112. By inserting the two end pieces 1141 and 1141' of the U-shaped hanging rod 114 of one scale element 11 into the transverse coupling holes 1123 and 1123' of another, the scale elements 11 are pivotably connected together (see FIG. 3B). When the scale elements 11 are coupled together, they can be folded up into a collapsed condition by turning one scale element about the end pieces 1141 and 1141' of the U-shaped hanging rod 114 of another (see FIG. 4). When the coupling block 111 of a first scale element 11 is pushed forwardly into the coupling open chamber 112 of a second scale element 11, the coupling tongues 1111 of the first scale element are respectively forced into engagement with the coupling grooves 1121 of the second scale element, and the balls 1125 of the retaining devices 1122 of the second scale element are respectively forced by the respective compression springs 1126 into engagement with the retaining grooves 1112 of the first scale element, and therefore the two scale elements 11 are longitudinally connected in a line in a flush manner (see FIG. 3C).

Referring to FIG. 2, the measurement indicator 2 comprises a sliding block 21, and an indicating bar 22. The sliding block 21 comprises a back sliding groove 211 slidably coupled to the longitudinal sliding tracks 113 of the scale 1, two forward lugs 23 and 23' perpendicularly raised from its front side near the top, two stub pivot rods 24 respectively and perpendicularly raised from the lugs 23 and 23' at an outer side, a socket 25 fixedly mounted in a through hole (not shown) between the lugs 23 and 23', a hook 212 raised from its front side above the barrel 25 and adapted for holding the indicating bar 22 in the indicating position perpendicular to the sliding block 21, a sealing cap 28 fastened to the socket 25, a compression spring 27 mounted in the socket 25 and supported on the sealing cap 28, and a ball 26 mounted in the socket 25 and supported on the compression spring 27 and forced by the compression spring 27 to partially project out of the socket 25 and stopped against the surface of the scale 1. By means of the friction resistance between the ball 26 and the surface of the scale 1, the sliding block 21 of the indicator 2 is stopped from sliding on the scale 1. The indicating bar 22 has two pivot holes 221 bilaterally disposed at its hollow, box-like rear end and respectively coupled to the stub pivot rods 24 of the lugs 23.

Figure 4:
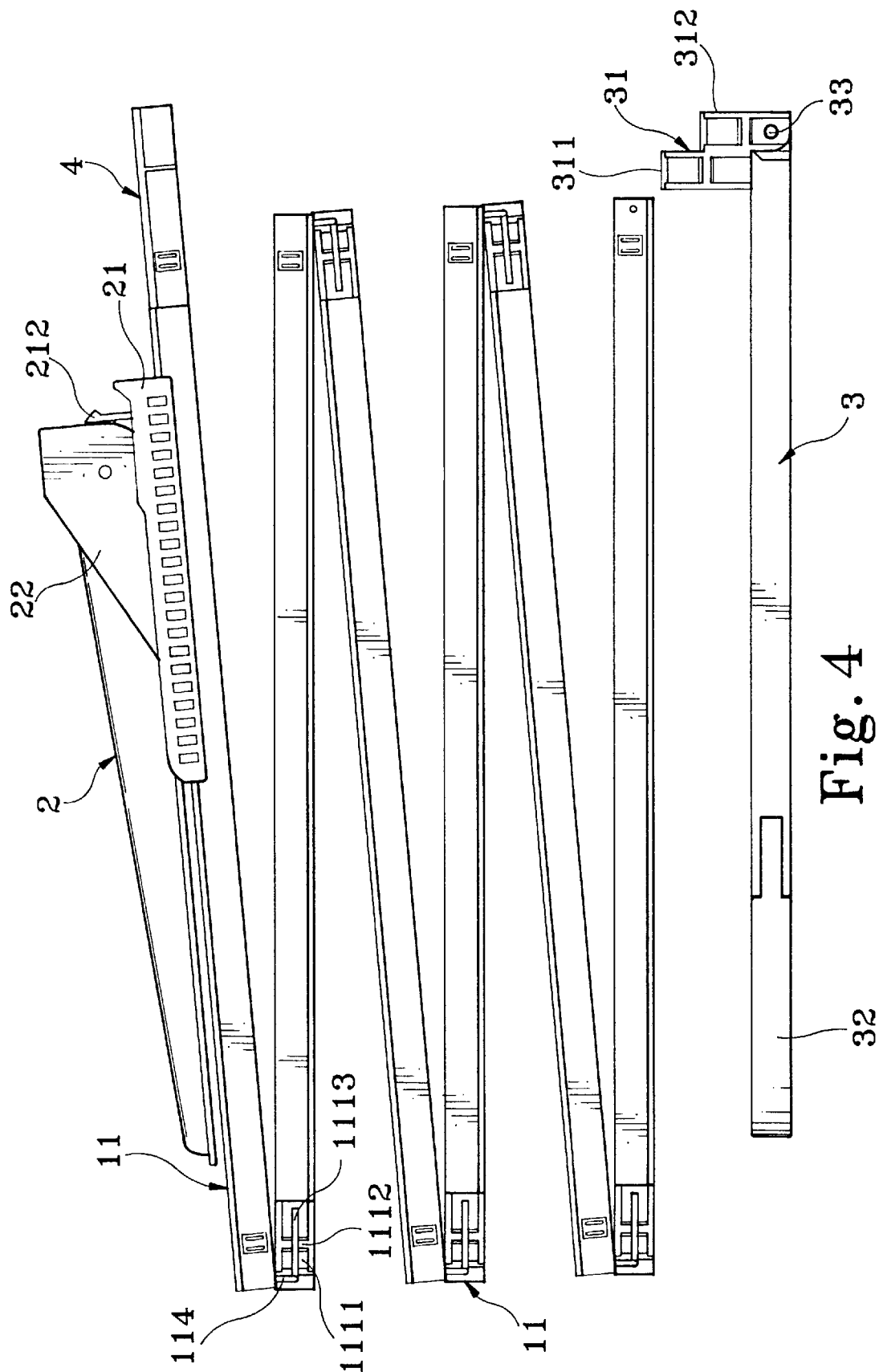
FIG. 4 shows the folding collapsible body-height measuring gauge folded up according to the present invention.

Referring to FIGS. 2 and 4, the base 31 comprises a coupling block 31 pivotably connected to its rear end by a pivot 33, and two legs 32 and 32' pivoted to its front end. The coupling block 31 comprises a front coupling portion 311 disposed above the top side of the base 31, and a rear coupling portion 312 having a bottom side disposed in flush with the bottom side of the base 31. The front coupling portion 311 and the rear coupling portion 312 have the same structure of the coupling block 111 of each scale element 11, and can be alternatively coupled to the coupling open chamber 112 of the bottom scale element 11. The legs 32 and 32' can be turned within 90° relative to each other between the operative position as shown in FIG. 1, and the collapsed position as shown in FIG. 6.

Referring to FIG. 1, when the scale 1 is coupled to the rear coupling portion 312 of the coupling block 31 of the base 3, the zero reading of the scale 1 starts from the bottom side of the base 1 (the ground), thus the body-height measuring gauge can be put on the ground in a vertical position for measuring the height of the body.

Figure 5:
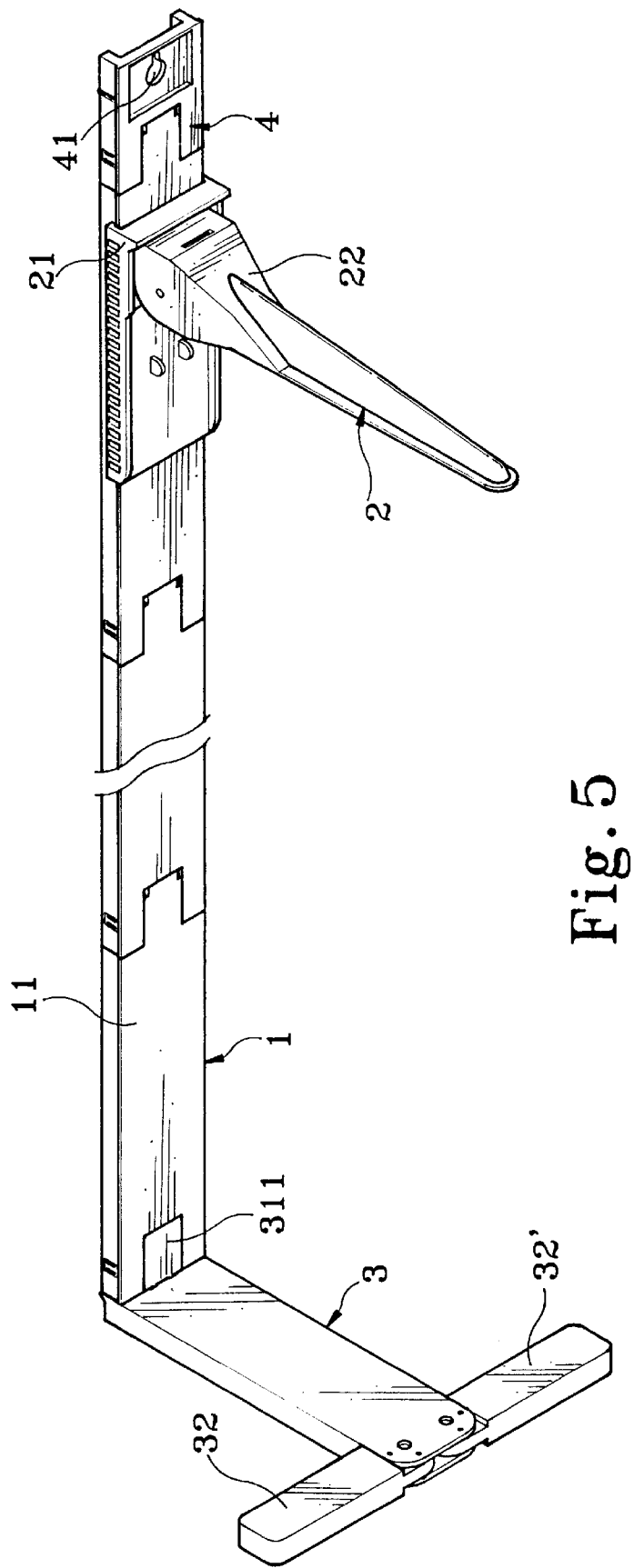
FIG. 5 shows the folding collapsible body-height measuring gauge set up and arranged for horizontal measurement.

Referring to FIG. 5, when the scale 1 is coupled to the front coupling portion 311 of the coupling block 31 of the base 3, the zero reading of the scale 1 starts from the top side of the base 3, thus the body-height measuring gauge can be put in a horizontal position to measure the height of the body of a baby or any person who cannot stand up.

Figure 6:
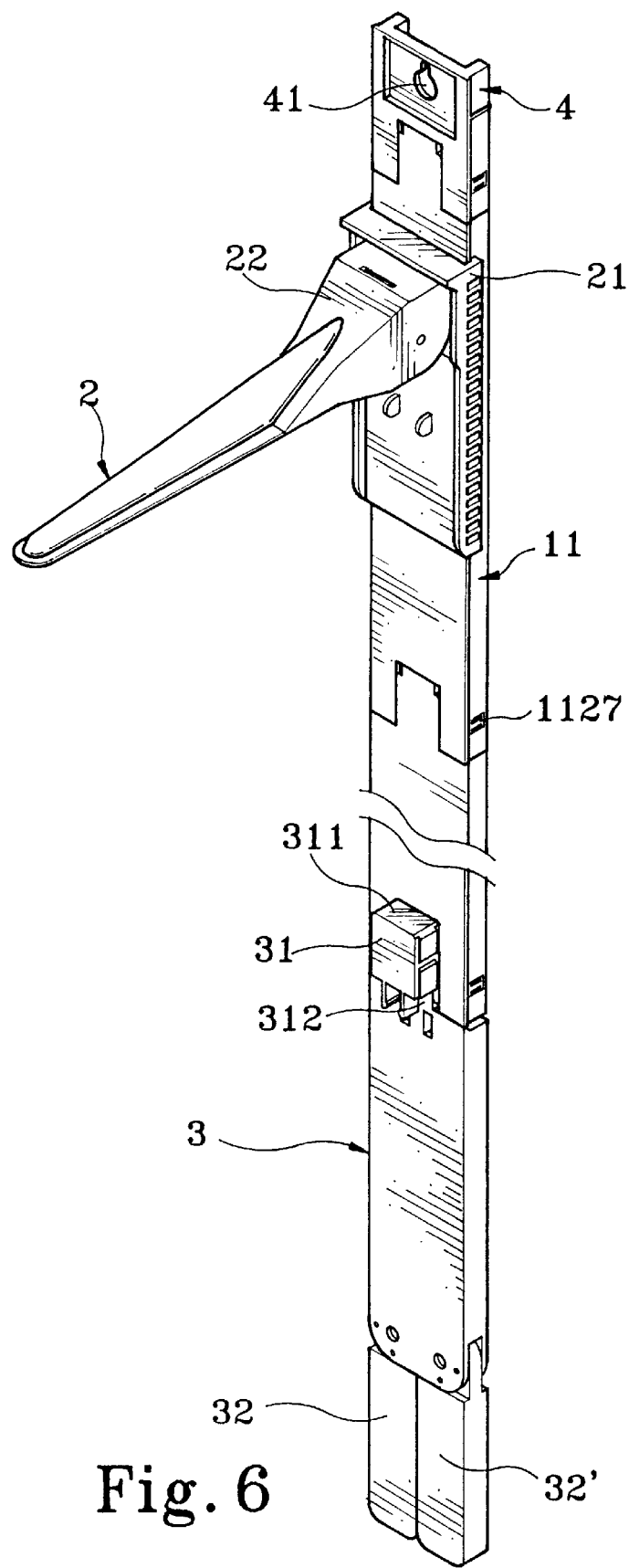
FIG. 6 is an applied view of the present invention, showing the base turned into longitudinal alignment with the scale.

Referring to FIG. 6, the hanging block 4 is coupled to the coupling block 111 of the top scale element 11, having a hanging hole 41 for hanging. Further, when the legs 32 and 32' are closed together, the coupling block 31 can be turned about the pivot 33 permitting the base 3 and the closed legs 32 and 32' to be moved into longitudinal alignment with the scale 1 to prolong the effective measuring length of the gauge.

I claim:

1. A folding collapsible body-height measuring gauge, comprising:

a scale having a plurality of scale elements pivotably connected with one another in a series by coupling portions, each scale element having two coupling portions disposed at different elevations and adapted for coupling to said scale alternately;

a measurement indicator longitudinally slidably mounted on said scale;

a base having a coupling block at one end coupled to said scale for supporting the scale in an operative position for measuring the height of the body;

said coupling portions of each of said scale elements including a respective coupling block at one end and a respective coupling open chamber at an opposite end, said scale elements being connected together by coupling the coupling block of one scale element to the coupling open chamber of another one of said scale elements;

each of said scale elements including two longitudinal coupling grooves bilaterally disposed within its coupling open chamber, and two retaining devices respectively mounted in said longitudinal coupling grooves for securing to the coupling block of an adjacent scale element, the coupling block of each scale element having two longitudinal coupling tongues longitudinally raised from two opposite sides thereof for engaging with the longitudinal coupling grooves of another one of said scale elements; and a substantially U-shaped hanging rod moveable in a longitudinal sliding slot in the coupling block of each scale element of said scale, each of the U-shaped rods having two end pieces horizontally extended outwards in opposite directions for coupling to respective transverse coupling holes in the longitudinal coupling grooves of another one of said scale elements.

2. The folding collapsible body-weight measuring gauge of claim 1, wherein said base comprises legs pivotably connected to one end thereof remote from its coupling block.

* * * * *